United States Patent
Long et al.

(10) Patent No.: US 10,788,450 B2
(45) Date of Patent: Sep. 29, 2020

(54) PREPARATION METHOD FOR AEROLYSIN NANOPORE AND APPLICATION THEREOF

(71) Applicant: EAST CHINA UNIVERSITY OF SCIENCE AND TECHNOLOGY, Shanghai (CN)

(72) Inventors: Yitao Long, Shanghai (CN); Chan Cao, Shanghai (CN); Yongxu Hu, Shanghai (CN)

(73) Assignee: EAST CHINA UNIVERSITY OF SCIENCE AND TECHNOLOGY, Shanghai (CN)

( * ) Notice: Subject to any disclaimer, the term of this patent is extended or adjusted under 35 U.S.C. 154(b) by 116 days.

(21) Appl. No.: 15/546,671

(22) PCT Filed: Jan. 8, 2016

(86) PCT No.: PCT/CN2016/070446
§ 371 (c)(1),
(2) Date: Jul. 27, 2017

(87) PCT Pub. No.: WO2016/119584
PCT Pub. Date: Aug. 4, 2016

(65) Prior Publication Data
US 2018/0067076 A1    Mar. 8, 2018

(30) Foreign Application Priority Data
Jan. 30, 2015   (CN) .......................... 2015 1 0047662

(51) Int. Cl.
*C12Q 1/6869*    (2018.01)
*G01N 33/487*    (2006.01)
*G01N 27/447*    (2006.01)

(52) U.S. Cl.
CPC ....... *G01N 27/4473* (2013.01); *C12Q 1/6869* (2013.01); *G01N 27/44791* (2013.01); *G01N 33/48721* (2013.01)

(58) Field of Classification Search
CPC ............ C12Q 1/6869; C12Q 2565/631; C12Q 2521/101; C12Q 2521/325;
(Continued)

(56) References Cited

U.S. PATENT DOCUMENTS 9,547,004 B2    1/2017  Durand
2005/0266512 A1*  12/2005  Buckley .................. C12Q 1/37
                                                          435/23

(Continued)

FOREIGN PATENT DOCUMENTS

CN    101799447    8/2010
CN    103502795    1/2014
(Continued)

OTHER PUBLICATIONS

Ying Yi Lun, Study of Biological Weak Interactions at Single-Molecule Level by Nanopore Technology, dissertation, Jun. 30, 2014, p. 2-3, 6-8, 16&21, Jun. 2014, China Doctoral Dissertations Full-text Database, Beijing China.
(Continued)

*Primary Examiner* — Mayla Gonzalez Ramos
(74) *Attorney, Agent, or Firm* — Mark M. Friedman

(57) ABSTRACT

A preparation method for an aerolysin nanopore in this disclosure comprises the following steps: (1) pretreatment of an aerolysin; (2) preparation of a lipid bilayer membrane by pulling process; (3) forming of the aerolysin nanopore: the aerolysin nanopore is obtained at a current of 50±5 pA. The aerolysin nanopore prepared in the invention is structurally stable and has a high resolution with the whole internal cavity carried with a positive charge, can be used for
(Continued)

detection without modification and is easily operated. Further, the aerolysin nanopore can be applied in DNA sequencing, DNA damage and Micro-RNA detection.

3 Claims, 7 Drawing Sheets

Specification includes a Sequence Listing.

(58) Field of Classification Search
CPC .......... C12Q 2521/543; C12Q 2527/15; C12Q 2527/156; C12Q 2537/164; G01N 33/48721; G01N 27/4473; G01N 27/44791; G01N 27/48721
See application file for complete search history.

(56) References Cited

U.S. PATENT DOCUMENTS

| | | | |
|---|---|---|---|
| 2009/0167288 A1* | 7/2009 | Reid | G01N 33/48721 324/72 |
| 2014/0064324 A1* | 3/2014 | Kasianowicz | G01K 7/16 374/45 |
| 2014/0203464 A1* | 7/2014 | Chen | G01N 15/12 264/40.1 |

FOREIGN PATENT DOCUMENTS

| | | |
|---|---|---|
| CN | 203572764 | 4/2014 |
| CN | 104254619 | 12/2014 |
| CN | 104651500 | 5/2015 |

OTHER PUBLICATIONS

Yi-Lun Ying, Chan Cao, Yi-Tao Long, Single molecule analysis by biological nanopore sensors, journal, Jun. 10, 2014, p. 3826-3835, 139(16), Analyst, England.

Aziz Fennouri, Regis Daniel, Manuela Pastoriza-Gallego, Loic Auvray, Juan Pelta, and Laurent Bacri, Kinetics of Enzymatic Degradation of High Molecular Weight Polysaccharides through a Nanopore: Experiments and Data-Modeling, journal, Aug. 30, 2013, p. 8488-8492, 85(18), Analylical Chemistry, Washington DC U.S.A.

Ying Yilun, Zhang Xing, Liu Yu, Xue Mengzhu, Li Honglin, Long Yitao, Single Molecule Study of the Weak Biological Interactions Between P53 and DNA, journal, Dec. 25, 2012, p. 44-50, 71, Acta Chimica Sinica, Shanghai China.

* cited by examiner

```
┌─────────────────────────────────────┐
│   Pretreatment of an aerolysin      │
└─────────────────────────────────────┘
                 ↓
┌─────────────────────────────────────┐
│ Preparation of a lipid bilayer      │
│ membrane by pulling process         │
└─────────────────────────────────────┘
                 ↓
┌─────────────────────────────────────┐
│   Preparing a phospholipid          │
│   n-decane solution                 │
└─────────────────────────────────────┘
                 ↓
┌─────────────────────────────────────┐
│      Smearing the                   │
│   phospholipid n-decane      ←──┐
│      solution                   │
└─────────────────────────────────┘  │
                 ↓                   │
┌─────────────────────────────────┐  │
│     Applying a potential        │  │
└─────────────────────────────────┘  │
                 ↓                   │
┌─────────────────────────────────┐  │
│     Pulling the solution        │  │
│        repeatedly               │  │
└─────────────────────────────────┘  │
                 ↓                   │
┌─────────────────────────────────┐  │
│     Testing and repetition      ├──┘
└─────────────────────────────────┘
                 ↓
┌─────────────────────────────────────┐
│  Forming of the aerolysin nanopore  │
└─────────────────────────────────────┘
```

FIG. 1

PREPARATION METHOD FOR AEROLYSIN NANOPORE AND APPLICATION THEREOF

FIELD OF THE INVENTION

This disclosure relates to the field of molecular detection and DNA sequencing, and more specifically to a preparation method for an aerolysin nanopore and application thereof.

BACKGROUND OF THE INVENTION

The biological nanopore is the most natural nano-device using the transmembrane channel, with the aperture generally being only 1~10 nm, it can only accommodate a single molecule (such as DNA, Micro-RNA, peptides, sugar) passing through the nanopore, so that a real-time, high-throughput and label-free ultra-sensitive analysis of individual molecules can be realized in an aqueous solution. Currently, the more frequently applied biological nanopores include α-hemolysin, MspA nanopore and SP1 nanopore. These nanopores can realize the ultra-sensitive analysis of the molecules. However, shortcomings still exist in these nanopores due to small intermolecular differences, such as the distinction of various single bases, the distinction among various Micro-RNAs and the testing of DNA damage, the speed of molecules passing through the nanopore is too fast and the resolution is not high enough.

In order to further improve the resolution of the nanopores, many studies have been devoted to the modification of α-hemolysin nanopores to shorten the effective pore size of the nanopores. For example, Bayley's group used genetic engineering, site-directed mutagenesis of α-hemolysin internal amino acids, and the incorporation of cyclodextrins to achieve the purposes of reducing pore size, thus resulting in the ultra-sensitive detection of small changes in molecules. However, realization of this technology needs mastery of gene mutation technology, but the workload is heavy and it is not easy to realize repetition and reproduction. In addition, other studies have been conducted focusing on reducing the speed of DNA molecules passing through the nanopore by way of changing the concentration of the electrolyte solution, introducing DNA polymerase, and gene mutations to positively charge the nanopores. In 2008, the MspA nanopore with a pore size of 1.2 nm was found, so the resolution of DNA detection significantly improved due to the shortened pore size of 0.2 nm relative to α-hemolysin. However, since the amino acid in the wild-type MspA channel is negatively charged, the pores without modification would result in a considerable background signals, the MspA channel cannot be used for the further nanopore analysis; therefore, MspA cannot be used as a method for nanopore analysis until the negative charge inside the pore is converted to a positive charge by way of gene mutation. This undoubtedly increases the difficulty in tests, and makes the experimental process more complex and difficult.

SUMMARY OF THE INVENTION

The objective of this disclosure is to solve the above-mentioned problems by providing a preparation method for an aerolysin nanopore which can self-assemble in solution to form a heptamer structure and be inserted into a lipid bilayer membrane through conformational changes to form a nano-sized channel, this nanopore with a natural structure has a smaller pore size and a better resolution, which shows a positive electronegativity in the inner cavity of the aerolysin nanopore, and can interact with the negatively charged molecules to slow down the translocation speed of the molecules. Therefore more small changes can be distinguished at the single molecule level to provide an ultra-sensitive resolution of a single base; the second objective of the disclosure is to provide a specific application of the aerolysin nanopore in DNA sequencing, DNA damage and Micro-RNA detection.

To achieve the purposes above, the disclosure adopts the following technical solution:

a preparation method for an aerolysin nanopore, characterized by comprising the following steps:

(1) pretreatment of an aerolysin, in which:

a trypsin-EDTA solution and the aerolysin are mixed at a ratio of 1:100 and incubated at room temperature for 10 min to activate the aerolysin, and the activated aerolysin is treated in a PBS buffer and stored in a refrigerator at −20° C. at a concentration ranging from 0.1 to 10 mgmi:

(2) preparation of a lipid bilayer membrane by pulling process, in which:

the lipid bilayer membrane is formed at a polyacetal resin chamber as a carrier, wherein the polyacetal resin chamber comprises chamber I (i.e., cis chamber) and chamber II (i.e., trans chamber), with the chamber II embedded in the chamber I; the polyacetal resin chamber is divided into two regions after the lipid bilayer membrane is formed: as the aerolysin nanopore is unidirectional when embedded into the lipid bilayer membrane, the region corresponding to a relatively large opening of the aerolysin nanopore embedded in the lipid bilayer membrane is defined as the chamber I while the other region, correspond to a relatively small opening of the aerolysin nanopore is defined as the chamber II; the chamber II provided with a small pore of with the diameter of 50 μm, wherein the small pore is configured for forming the lipid bilayer membrane; the chamber I is provided in a lateral side thereof with a pulling pore in communication with an interior of the chamber I, wherein the pulling pore is configured for insertion by an injector for pulling an internal solution; and a 1,2-diglycanoyl phospholipid to be used for forming the lipid bilayer membrane is stored in a chloroform solution in a refrigerator at −20° C.; the step of preparation of the lipid bilayer membrane more specifically comprising the sub-steps of:

(a) preparation of a phospholipid n-decane solution, drying the chloroform in the 1,2-diglycanoyl phospholipid chloroform solution and adding 90 μl of n-decane into the chloroform-removed 1,2-diglycanoyl phospholipid to prepare a phospholipid n-decane solution, prior to the step of preparation of the lipid bilayer membrane.

(b) smearing of the phospholipid n-decane solution, smearing the phospholipid n-decane solution evenly on both internal and external sides of the small pore of the chamber 2 (1 mL) with a sable paint brush and drying the phospholipid n-decane solution with a flow of $N_2$ to form a lipid bilayer membrane:

(c) application of potential, putting the chamber I and the chamber II together, adding 1 mL of an electrolyte solution into each the chamber, immersing a pair of AgiAgCl electrodes into the electrolyte solution, and applying a potential of 100 mV across lipid bilayer membrane via output ends ofa current amplifier, wherein the cis chamber is defined as a virtual ground;

(d) pulling the electrolyte solution repeatedly to form the lipid bilayer membrane at the small pore of the trans chamber; monitoring the quality of the formed lipid bilayer membrane via capacitance, applying a potential of 400 mV to examine the mechanical strength of the lipid bilayer during formation of the lipid bilayer membrane;

If the lipid bilayer membrane is broken, pull the electrolyte to form another lipid bilayer membrane, the capacitance of the another lipid bilayer membrane will be equal to or higher than the capacitance of the broken lipid bilayer membrane such that the another lipid bilayer membrane is capable of forming a nanopore; and if the capacitance of the another lipid bilayer membrane is reduced, the potential of 400 mV is persistently applied; and (e) testing and repetition, if the lipid bilayer membrane does not break under the potential of 400 mV, brushing the lipid bilayer membrane with a sable paint brush till the lipid bilayer membrane breaks, further, pulling the electrolyte to form a new lipid bilayer membrane, and then repeating the sub-steps (c) and (d) till a lipid bilayer membrane capable of forming a nanopore is obtained; and (3) formation of the aerolysin nanopore, in which:

1-10 μl of the aerolysin is added into the cis chamber after a stable the lipid bilayer membrane is formed, and a potential is applied to embed the aerolysin into the lipid bilayer membrane. The ionic current increases abruptly when the aerolysin forms a stable nanopore in the lipid bilayer membrane. At the same time, the aerolysin nanopore at a current of 50±5 pA under a potential of 100 mV can be obtained.

Furthermore, the range of the potential applied in Step (3) is 100-300 mV.

Furthermore, more than one nanopore can be obtained simultaneously via the preparation method, wherein the insertion of a nanopore corresponds to the current increase of 50±5 pA under a potential of 100 mV.

To achieve the purposes above, the disclosure adopts the following technical solution:

the application of the aerolysin nanopore in DNA sequencing, DNA damage, and Micro-RNA detection.

Furthermore, the application of the aerolysin nanopore in DNA sequencing, DNA damage and Micro-RNA detection is as follows:

(1) a potential is applied across the nanopore, and the analyte is added to one side of the chamber. The analyte is driven into the aerolysin nanopore and interacts with the aerolysin nanopore to generate a blocking current signal corresponding to its structural variation;

(2) changing the potential applied across the aerolysin nanopore, and recording the blocking current signal generated at different potentials;

(3) by making a statistic on the duration time, blocking current and signal frequency of recorded signals, the information about the analyte can be obtained.

All measured blocking current signals (blockade events) in the detection application involve two parameters: blocking current and duration time. A complete blockade event includes a cycle where the blocking current phase-steps and returns from the open pore current at a certain magnitude of the quantization to the open pore current till the next block event occurs, Therefore, there are four related test parameters: duration times (t), blocking current (i), event frequency (f) and peak shape. These four test parameters directly reflect the process of a single molecule passing through the aerolysin nanopore. Through the statistical analysis of blockade events, it is possible to obtain the information such as configuration, charge, translocation dynamics, translocation speed, and concentration of the target analyte. The changes in the detection conditions, such as molecular length, molecular conformation, applied potential, buffer concentration, pH, and temperature, will effect these four test parameters.

Furthermore, the application of the aerolysin nanopore in DNA sequencing, DNA damage, and Micro-RNA detection enables single base resolution, that is, DNA sequences (such as AGA, GGA, CGA and TGA) having only one base difference can be distinguished.

Furthermore, the application of the aerolysin nanopore in DNA sequencing, DNA damage, and Micro-RNA detection enables DNA sequencing: the inner diameter of the aerolysin nanopore can be smaller and have a higher resolution for single base by embedding the γ-cyclodextrin into the aerolysin nanopore.

Furthermore, the application of the aerolysin nanopore in DNA sequencing, DNA damage, and Micro-RNA detection enables DNA sequencing: different combinations of four bases are detected by taking four bases as a unit, and the DNA sequence is determined according to the characteristic current value corresponding to each combination.

Furthermore, the application of the aerolysin nanopore in DNA sequencing, DNA damage, and Micro-RNA detection, the DNA cleavage enzyme is ligated at the mouth of aerolysin nanopore, and the determination and cleavage of DNA is realized at the same time in the process that DNA passes through the aerolysin nanopore.

Furthermore, the application of the aerolysin nanopore in DNA sequencing, DNA damage, and Micro-RNA detection, the phi29 DNA polymerase is bound at the mouth of aerolysin nanopore, and DNA interacts with the phi29 DNA polymerase when entering into the aerolysin nanopore which reduces the speed of the DNA passing through the nanopore.

Furthermore, the application of the aerolysin nanopore in DNA sequencing, DNA damage, and Micro-RNA detection realizes the detection of DNA damage including the replacement, disappearance and insertion of the base, which is specifically divided into:

(1) the tautomerism of the base, such as the mismatch by tautomerism between the enol and the keto bases;

(2) the deamination of the base, that is, the exocyclic amino of the base will spontaneously fall off, so that the cytosine will become the uracil, the adenine will become the hypoxanthine (H), and the guanine will become the xanthine (X);

(3) depurination and depyrimidination, the spontaneous hydrolysis can make the purine and the pyrimidine fall from the DNA-chain ribosyl phosphate skeleton;

(4) base modification and chain breakage, the cell respiration not only generates the thymine glycol, hydroxymethyl uracil and other base modifiers, but also may cause structural changes such as the breakage of DNA single chain and other damage, the methylation inside DNA and hydroxymethylation;

(5) base alkylation caused, the loss of base and the breakage of the DNA chain by the alkylating agent.

Furthermore, the application of the aerolysin nanopore in DNA sequencing, DNA damage, and Micro-RNA detection can be used for the detection of different lengths of the telomere; the telomere consists of DNA sequences, with its length associated with the human life, and through this method different DNA sequences can be identified for the detection of different lengths of the telomere.

Furthermore, the application of the aerolysin nanopore in DNA sequencing, DNA damage, and Micro-RNA detection can be used for the label free detection of various Micro-RNAs; the Micro-RNA plays a role in adjusting the human gene expression, and the level of the Micro-RNA in the human body is directly related to various diseases; through the application of the detection provided in the disclosure, the level of Micro-RNA in actual samples can be detected at the single molecule level specificity without labeling for the clinical diagnosis of diseases.

The beneficial effects of the disclosure are as follows:

(1) the prepared aerolysin nanopore is structurally stable, and the resulting aerolysin nanopore can maintain its stable open-pore state for a long time without the interference caused by changes in external conditions, and the property can be stable in a denaturant with a high concentration;

(2) high resolution, the aerolysin has a naturally small diameter, a better resolution compared with other pores can be obtained without modification or amino acid mutation;

(3) the whole internal cavity carried with a positive charge enables the action between the negatively charged DNA molecules and the internal cavity of the aerolysin nanopore, which can reduce the speed of DNA strands passing through the nanopore. This provides a potential for the realization of the single base resolution.

(4) the disclosure can be used for detection without modification and is easily operated.

BRIEF DESCRIPTION OF THE DRAWINGS

FIG. 1 shows the flow of process for the preparation of the aerolysin nanopore in the disclosure;

The reference numbers in figures are as follows: 1. cis chamber; 2. pulling pore; 3. trans chamber; 4. small pore; 5. polyacetal resin chamber; 6. electrolyte solution; 7. lipid bilayer membrane; 8. cyclodextrin; 9. cleavage enzyme; 10. single nucleotide; 11. template chain; 12. primer chain; 13. oligomeric DNA chain; 14. DNA polymerase.

DESCRIPTION OF THE INVENTION

Specific embodiments of the preparation method for an aerolysin nanopore in the disclosure are described with reference to the accompanying drawings as follows, with five embodiments and seven application examples provided. Notably, however, the implementation of the disclosure is not limited to the following embodiments.

Embodiment 1

Figure 2:
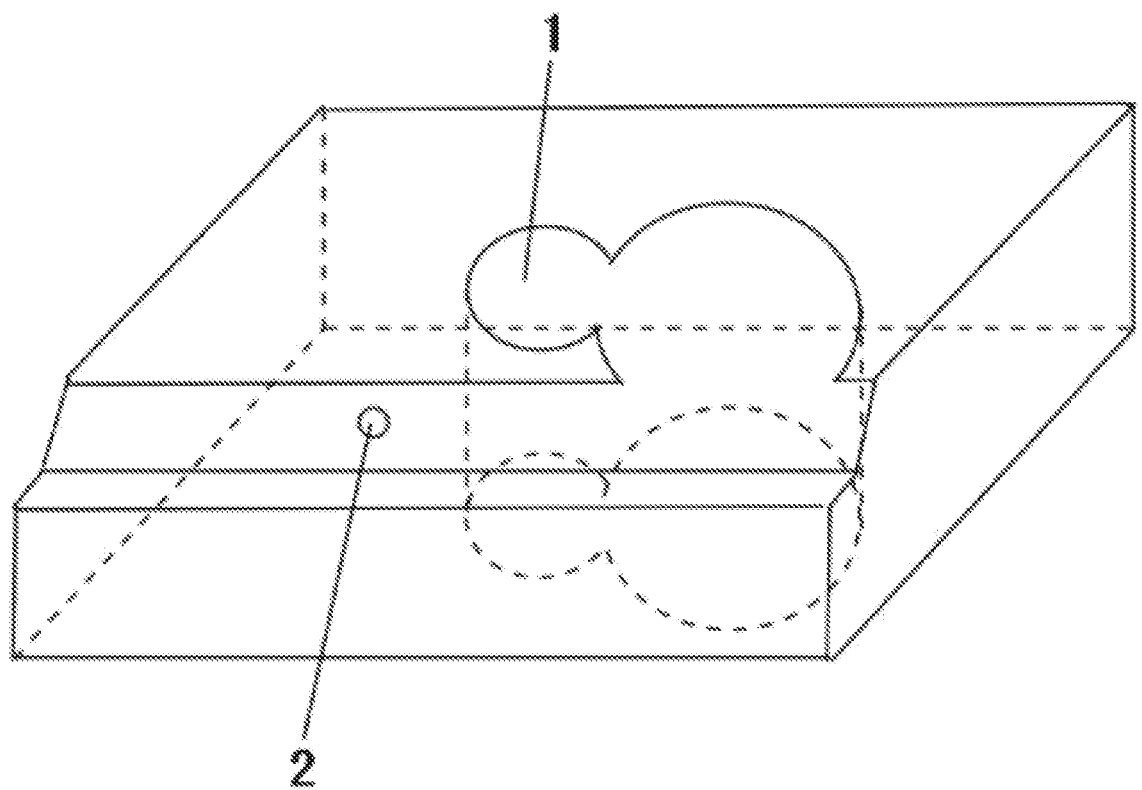
FIG. 2 shows the structure of chamber I.
Figure 3:
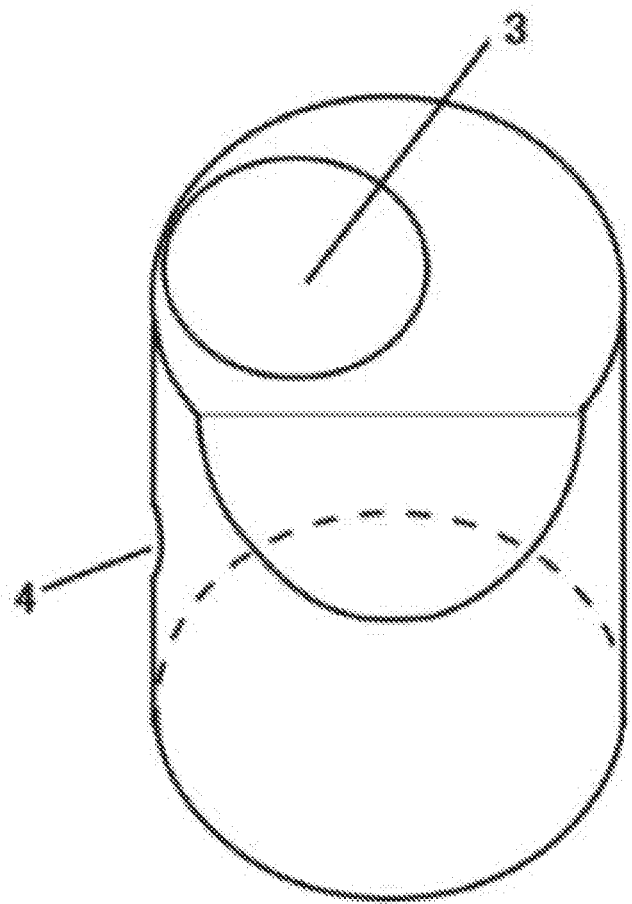
FIG. 3 shows the structure of chamber II.
Figure 4:
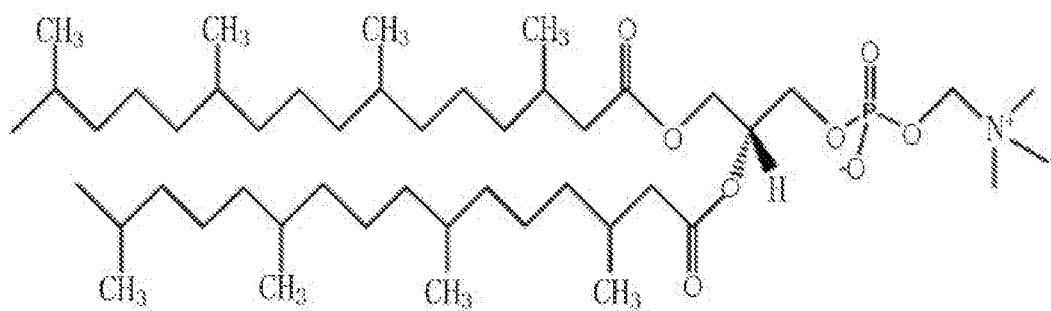
FIG. 4 shows the molecular structure of 1,2-dicarboxylic acid phospholipids.
Figure 5:
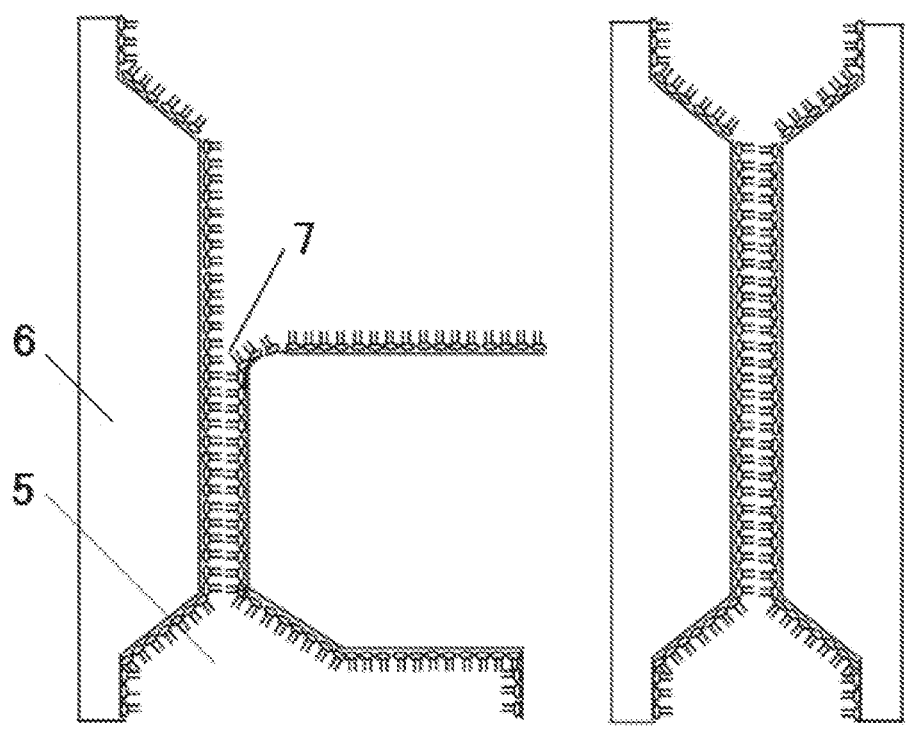
FIG. 5 shows the pulling principle.

Referring to FIG. 1: a preparation method for an aerolysin nanopore comprises the following steps:

(1) pretreatment of an aerolysin, in which:

a trypsin-EDTA solution and the aerolysin are mixed at a ratio of 1:100 and incubated at room temperature for 10 min for activating the aerolysin, and the activated aerolysin is treated in a PBS buffer and stored in a refrigerator at $-20°$ C. at a concentration of 0.1 mgiml;

(2) preparation of a lipid bilayer membrane by pulling process, in which:

the lipid bilayer membrane 7 is formed at a polyacetal resin chamber 5 as a carrier, wherein the polyacetal resin chamber 5 comprises chamber I (i.e., cis chamber 1, as shown in FIG. 2) and chamber II (i.e.,trans chamber 3, as shown in FIG. 3), with the chamber II embedded in the chamber I; the polyacetal resin chamber 5 is divided into two regions after the lipid bilayer membrane 7 is formed: as the aerolysin nanopore is unidirectional when embedded into the lipid bilayer membrane, the region corresponding to a relatively large opening of the aerolysin nanopore embedded in the lipid bilayer membrane is defined as cis chamber 1 (i.e. the chamber I) while the other region, correspond to a relatively small opening of the aerolysin nanopore is defined as trans chamber 3 (i.e.,the chamber II); the chamber II provided with a small pore 4 of with the diameter of 50 μm, wherein the small pore is configured for forming the lipid bilayer membrane 7; the chamber I is provided in a lateral side thereof with a pulling pore 2 in communication with an interior of the chamber I, wherein the pulling pore 2 is configured for insertion by an injector for pulling an internal solution; and a 1,2-diglycanoyl phospholipid to be used for forming the lipid bilayer membrane 7 is stored in a chloroform solution in a refrigerator at $-20°$ C.; the step of preparation of the lipid bilayer membrane more specifically comprises the sub-steps of:

(a) smearing of the phospholipid n-decane solution: removing the chloroform in the 1,2-diglycanoyl phospholipid chloroform solution and adding 90 μl of n-decane into the chloroform-removed 1,2-diglycanoyl phospholipid to prepare a phospholipid n-decane solution, prior to the step of preparation of the lipid bilayer membrane;

(b) smearing of the phospholipid n-decane solution: smearing the phospholipid n-decane solution evenly on both internal and external sides of the small pore 4 of the chamber II (lmL) with a sable paint brush and drying the applied phospholipid n-decane solution with a flow of $N_2$ to form a lipid bilayer membrane;

(c) application of potential, putting the chamber I and the chamber II together, adding 1 mL of an electrolyte solution 6 into each the chamber, immersing a pair of Ag/AgCl electrodes into the electrolyte solution 6, and applying a potential of 100 mV across lipid bilayer membrane 7 via output ends ofa current amplifier, wherein the cis chamber I is defined as a virtual ground;

(d) pulling the electrolyte solution repeatedly (the pulling principle is as shown in FIG. 5) to form the lipid bilayer membrane at the small pore 4 of the trans chamber 3; monitoring the quality of the formed lipid bilayer membrane 7 via capacitance, applying a potential of 400 mV to examine the mechanical strength of the lipid bilayer during formation of the lipid bilayer membrane. If the lipid bilayer membrane is broken, pull the electrolyte to form another lipid bilayer membrane, the capacitance of the another lipid bilayer membrane will be equal to or higher than the capacitance of the broken lipid bilayer membrane such that the another lipid bilayer membrane is capable of forming a nanopore; and if the capacitance of the another lipid bilayer membrane is reduced, the potential of 400 mV is persistently applied; and (e) testing and repetition, if the lipid bilayer membrane does not break under the potential of 400 mV, brushing the lipid bilayer membrane with a sable paint brush till the lipid bilayer membrane breaks, further, pulling the electrolyte to form a new lipid bilayer membrane, and then repeating the sub-steps (c) and (d) till a lipid bilayer membrane capable of forming a nanopore is obtained; and (3) formation of the aerolysin nanopore, in which:

10 μl of the aerolysin is added into the cis chamber 1 after a stable lipid bilayer membrane is formed, and a potential of 100 mV is applied to embed the aerolysin into the lipid bilayer membrane. The ionic current increases abruptly when the aerolysin forms a stable nanopore in the lipid bilayer membrane. At the same time, the aerolysin nanopore at a current of 50±5 pA under a potential of 100 mV can be obtained.

The detection analysis on the prepared aerolysin nanopore in Embodiment 1:

To determine whether the resulting aerolysin nanopore can be used for detection, firstly we should check whether the displayed current value of the prepared aerolysin nanopore remains in the normal range, that is, the current value corresponding to a single nanopore at a potential of 100 mV is at 50±5 pA; second, the time-current curve without analyte at a different potential of (−200 mV~+200 mV) should be recorded after the preparation of the aerolysin nanopore, so as to determine whether the resulting aerolysin nanopore is stable, the stability of the recorded time-current curve means the resulting aerolysin nanopore can be used for detection.

Embodiment 1: the results of the detection analysis on the prepared aerolysin nanopore show that the aerolysin can be used for detection applications.

Embodiment 2

A method for preparing an aerolysin nanopore comprises the following steps:

(1) pretreatment of an aerolysin, substantially consistent with Embodiment 1; the difference is that the stored concentration of aerolysin after activation is 10 mg/ml.

(2) preparation of a lipid bilayer membrane by pulling process (consistent with Embodiment 1).

(3) formation of the aerolysin nanopore, substantially consistent with Embodiment 1; the difference is that 1 μl of the aerolysin is added into the cis chamber 1 after a stable lipid bilayer membrane is formed, and a potential of 200 mV is applied to embed the aerolysin into the lipid bilayer membrane, wherein an ionic current increases abruptly when the aerolysin forms a stable nanopore in the lipid bilayer membrane, and wherein the aerolysin nanopore is obtained at a current of 100±5 pA under a potential of 200 mV.

For Embodiment 2, the detection and analysis of the prepared aerolysin nanopore are substantially consistent with Embodiment 1.

The potential is adjusted to 100 mV to verify whether the current of the aerolysin nanopore prepared in Embodiment 2 is in the range of 50±5 pA.

Embodiment 3

A method for preparing an aerolysin nanopore comprises the following steps:

(1) pretreatment of an aerolysin, substantially consistent with Embodiment 1; the difference is that the stored concentration of aerolysin after activation is 1.5 mg/ml.

(2) preparation of a lipid bilayer membrane by pulling process (consistent with Embodiment 1).

(3) formation of the aerolysin nanopore, substantially consistent to Embodiment 1; the difference is that 3 μl of the aerolysin is added into the cis chamber 1 after a stable lipid bilayer membrane is formed, and a potential of +300 mV is applied to embed the aerolysin into the lipid bilayer membrane, wherein an ionic current increases abruptly when the aerolysin forms a stable nanopore in the lipid bilayer membrane, and wherein the aerolysin nanopore is obtained at a current of 150±5 pA under a potential of 300 mV.

For Embodiment 3, the detection and analysis of the prepared aerolysin nanopore are substantially consistent with Embodiment 1.

The potential is adjusted to 100 mV to verify whether the current of the aerolysin nanopore prepared in Embodiment 3 is in the range of 50±5 pA.

Embodiment 4

A method for preparing an aerolysin nanopore comprises the following steps:

(1) pretreatment of an aerolysin, substantially consistent with Embodiment 1; the difference is that the stored concentration of aerolysin after activation is 0.5 mg/ml;

(2) preparation of a lipid bilayer membrane by pulling process (consistent with Embodiment 1);

(3) formation of the aerolysin nanopore (substantially consistent to Embodiment 1); the difference is that 5 μl of the aerolysin is added into the cis chamber 1 after a stable lipid bilayer membrane is formed, and a potential of 150 mV is applied to embed the aerolysin into the lipid bilayer membrane, wherein an ionic current increases abruptly when the aerolysin forms a stable nanopore in the lipid bilayer membrane, and wherein the aerolysin nanopore is obtained at a current of 75±5 pA under a potential of 150 mV.

For Embodiment 4, the detection and analysis of the prepared aerolysin nanopore are substantially consistent with Embodiment 1.

The potential is adjusted to 100 mV to verify whether the current of the aerolysin nanopore prepared in Embodiment 4 is in the range of 50±5 pA.

Embodiment 5

A method for preparing an aerolysin nanopore comprises the following steps:

(1) pretreatment of an aerolysin, substantially consistent with Embodiment 1; the difference is that the stored concentration of aerolysin after activation is 1.5 mg/ml;

(2) preparation of a lipid bilayer membrane by pulling process (consistent with Embodiment 1);

(3) formation of the aerolysin nanopore, substantially consistent with Embodiment 1; the difference is that 3 μl of the aerolysin is added into the cis chamber 1 after a stable lipid bilayer membrane is formed, and a potential of 100 mV is applied to embed the aerolysin into the lipid bilayer membrane, wherein an ionic current increases abruptly when the aerolysin forms a stable nanopore in the lipid bilayer membrane, and wherein the aerolysin nanopore is obtained at a current of 150±5 pA under a potential of 100 mV.

For Embodiment 5, the detection and analysis of the prepared aerolysin nanopore are substantially consistent with Embodiment 1.

Application Example 1

Figure 6:
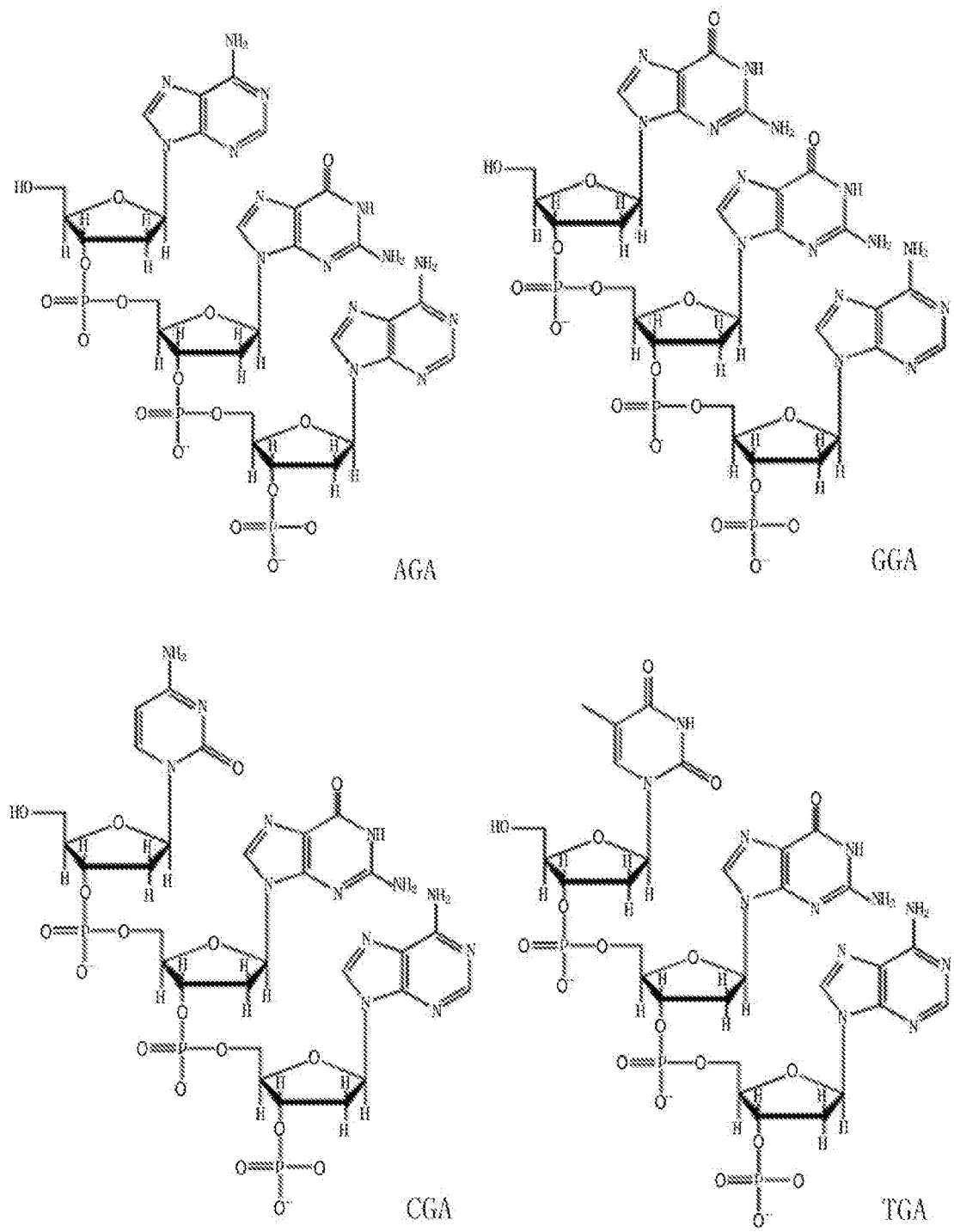
FIG. 6 shows a schematic representation of a single base for the DNA sequence with a different base.

Single base discrimination can be carried out via an aerolysin nanopore as follows:

(1) a potential is applied across the nanopore, and a single stranded DNA with only one different base site is added to one end of the polyacetal resin chamber 5, wherein the sequence may be AGA, GGA, CGA, TGA; or AAA, TAA, CAA, GAA, or any other DNA sequence having a different length and a different base site. An applicable DNA sequence is shown in FIG. 6. The single stranded DNA is driven into the aerolysin nanopore by an ionic current and interacts with the aerolysin nanopore to generate a blocking current signal corresponding to the structural variation;

(2) changing the potential applied across the aerolysin nanopore, and recording the blocking current signal generated at different potentials;

(3) by performing a statistical analysis on the blocking extent of the collected signals (i.e., the ratio of the blocking current to the open pore current), DNA sequences containing different bases can be clearly distinguished. Furthermore, the difference between a single or multiple bases resulting from DNA damage could be detected.

Application Example 2

The DNA sequencing can be carried out by way of adding a cleavage enzyme into the mouth of aerolysin nanopore as follows:

(1) for any DNA sequence, four base sequences are taken as a unit, so there have a total of 64 arrangements, with each corresponding to a characteristic blocking current value. 64 kinds of DNA sequences with different arrangements are added into cis chamber 1 of the polyacetal resin chamber 5 respectively, and the corresponding blocking current values are counted for each arrangement;

(2) a length of the single stranded DNA to be detected is added into cis chamber 1, the single stranded DNA would be cleaved by taking four bases as a unit under the action of the cleavage enzyme and falls into the aerolysin nanopore to generate its characteristic blocking current value;

(3) the detected single-stranded DNA sequence can be obtained by comparing the blocking current value generated in Step (2) with the 64 blocking current values measured in Step (1).

Application Example 3

Figure 7:
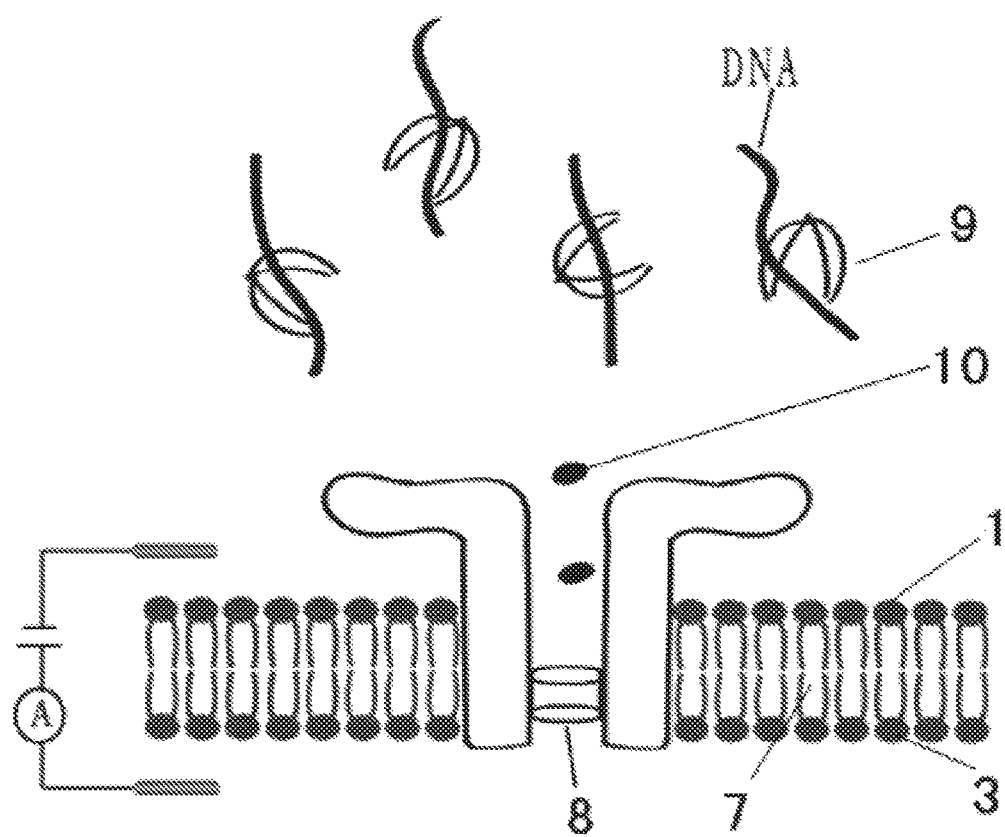
FIG. 7 shows a schematic representation of DNA sequencing by way of embedding the cyclodextrin.

The DNA sequencing can be carried out by embedding cyclodextrin into the aerolysin nanopore, with the experimental principle as shown in FIG. 7.

(1) The γ-cyclodextrin 8 is added from cis chamber 1 or trans chamber 3, and the γ-cyclodextrin 8 can be embedded into the aerolysin nanopore so that the effective inner diameter of the aerolysin nanopore is smaller.

(2) After the γ-cyclodextrin 8 is embedded, the open pore current decreases, and at this time, four bases of A, T, C and G are added respectively; the cyclodextrin 8 modified aerolysin nanopore can generate different characteristic currents for the four bases of A, T, C and G.

(3) The DNA cleavage enzyme 9 is added into cis chamber 1 of the polyacetal resin chamber 5, and then the single stranded DNA to be detected is added; the single stranded DNA to be detected can be cleaved by the DNA cleavage enzyme 9 into single bases (single nucleotides 10) and can be detected sequentially in the aerolysin nanopore that the cyclodextrin 9 is embedded.

(4) To make the cleavage enzyme 9 close to the mouth of the nanopore in the detection, the method for applying the salt concentration gradient at both ends of the aerolysin nanopore is conducted; the concentration of potassium chloride in cis chamber 1 and trans chamber 3 is 250 mM and 500 mM respectively, and the electrolyte solution at both ends contains 25 mM of Tris-HCl respectively, with the pH adjusted to 7.9.

Application Example 4

The DNA sequencing can be carried out by way of binding the phi29 DNA polymerase 14 to the aerolysin nanopore.

As one member of the β-family polymerase, the phi29 DNA polymerase 14 can rotate the single strand DNA enter into the nanopore like a gear, and each DNA chain extends into the nanopore in the polymerase proofing process and exits out of the nanopore in the DNA polymerizing process, so as to realize the secondary detection of each nucleotide in the nanopore and improve the time resolution and the accuracy of the DNA sequencing.

(1) The phi29 DNA polymerase 14 is added into cis chamber 1 and a DNA chain containing the DNA sequence to be read is added additionally; this DNA chain comprises a template chain 11 containing a sequence to be read, a primer chain 12 and a oligomeric DNA chain 13, wherein the primer chain 12 has a length of hairpin structure on its 5'-phosphate end to prevent the phi29 DNA polymerase from reacting with the double-stranded end of the DNA after complementary pairing. The oligomeric DNA chain 13 and the template chain 11 both contain abasic residues and thus can be identified through the changes of current at the two ends of the DNA sequence.

(2) 10 mM of the magnesium chloride and 100 uM of dCTP, dATP, dTTP and dGTP each are added into cis chamber 1 of the polyacetal resin chamber 5 for DNA synthesis; the detection should be conducted at room temperature.

Figure 8:
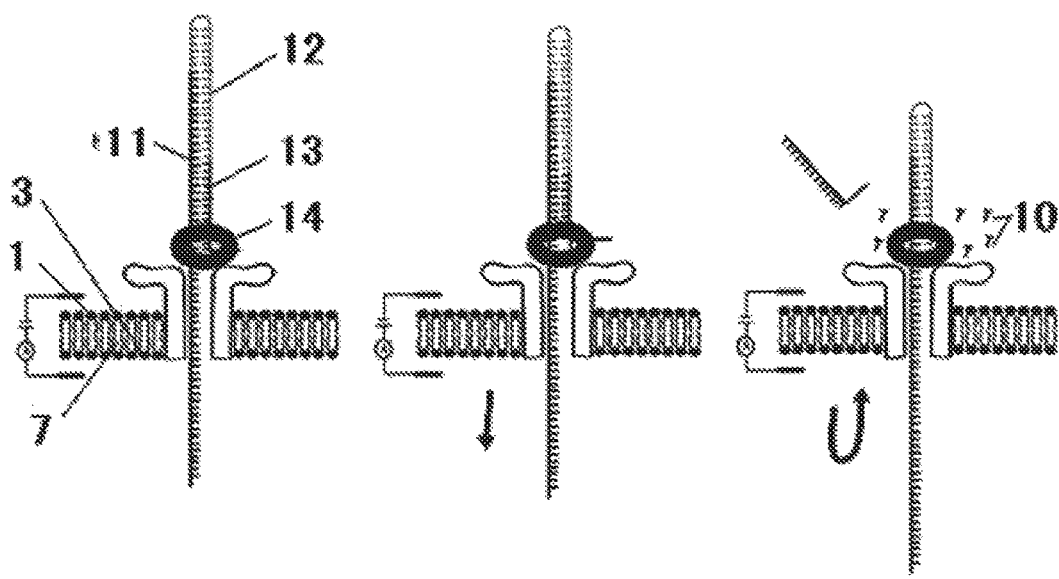
FIG. 8 shows the structure of the cytosine before and alter the methylation.

(3) The principle of DNA sequencing with the phi29 DNA polymerase 14 is shown in FIG. 8: the template chain 11 firstly enters into the nanopore, and in the process of further entry; the oligomeric DNA chain 13 is slowly desorbed with the template chain 11, unzipping the oligomeric DNA chain 13, then, the oligomeric DNA chain 13 is removed when it comes to the base-free site and reverse the direction. The hairpin structure of the primer chain 12 at the end of the 5'-phosphate prevents the phi29 polymerase from further reacting with double-chain DNA. At the same time, the dCTP, dATP, dTTP and dGTP in the polyacetal resin chamber 5 are paired with the template chain 11 and polymerized onto the oligomeric DNA chain 13 under the action of the phi29 DNA polymerase 14, and simultaneously make the oligomeric DNA chain 13 move in the reverse direction; the polymerization slows down the speed of the oligomeric DNA strand 13 passing through the nanopore which realizes the discrimination of single bases.

Application Example 5

DNA damage can be detected via an aerolysin nanopore.

Figure 9:
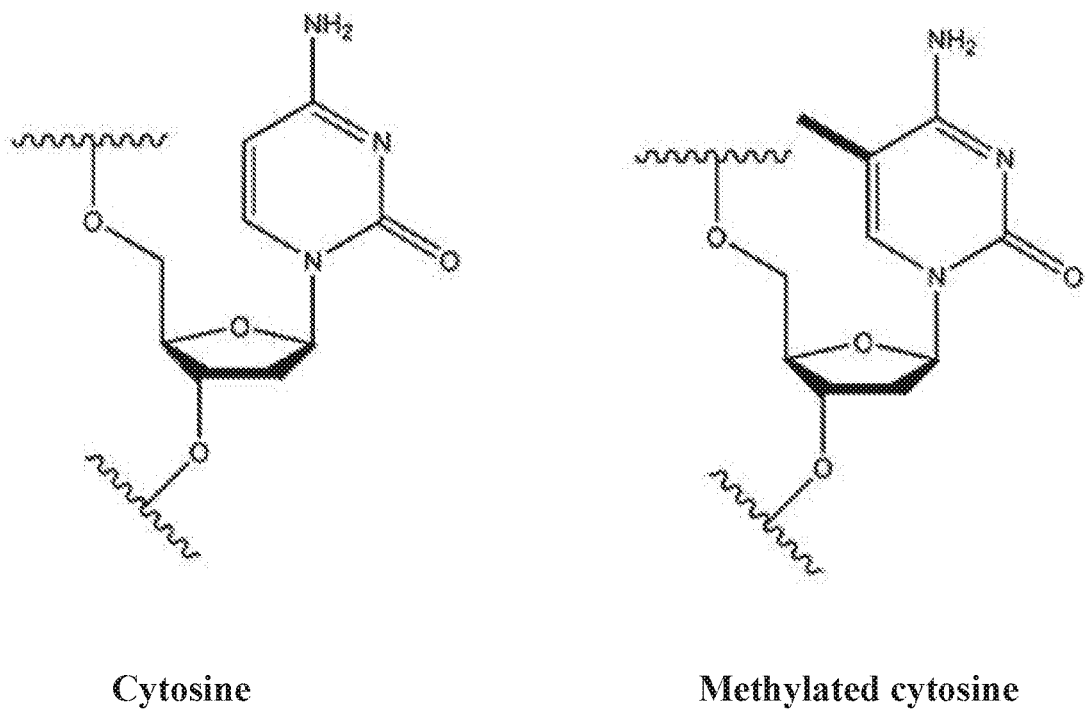
FIG. 9 shows a schematic representation of DNA sequencing with the phi29 DNA polymerase.

(1) Methylation of DNA, one embodiment is the methylation of cytosine, and the cytosine structure before and after methylation is shown in FIG. 9.

(2) The CG DNA sequence containing the unmethylated cytosine is added into the chamber separately.

(3) The DNA sequences containing the unmethylated and methylated cytosines are mixed at a ratio of 1:1 and added into the chamber.

(4) By performing a statistical analysis on the signals obtained from Steps (1), (2) and (3), it should be understood that two DNA sequences can be distinguished via the aerolysin nanopore in the disclosure, so that the peak value of the blocking current when the DNA sequences are added upon mixture can well correspond to that of the blocking current when the DNA sequences are added separately.

Application Example 6

The telomere detection can be carried out via an aerolysin nanopore.

The "telomere" is a small portion of the DNA-protein complex present at the end of the linear chromosome of the eukaryotic cell, which together with the telomere binding protein constitutes a special "hat" structure that retains the integrity of the chromosome. The telomere DNA is composed of the simple DNA-highly-repetitive sequences, and the telomerase can be used for tailing of the telomere DNA; once DNA molecules split and replicate each time, the telomere will shorten (such as Okazaki fragments). When the telomere is exhausted, the chromosomes are susceptible to mutations which may lead to arteriosclerosis and certain cancers. So the length of the telomere can reflect the history of cell replication and the replication potential, which is known as the "mitotic clock" of the cell life. The human telomere DNA sequence is composed of repeated units of n TTAGGG sequences. Different ages corresponding to different lengths of telomeres so as to correspond to the signals with different characteristics. According to this principle, people can detect the telomeres in different age groups and detect their corresponding blockade current and duration times, so as to obtain the distribution of human telomere lengths in different ages.

The step of detection more specifically comprises the sub-steps of:

(1) different age groups of human cells are taken, and the telomere DNA sequence at the end of its chromosome is extracted, by biological means. Taking 10 years of age as a span, that is, the telomeres in human bodies of people aged 0, 10, 20, 30, 40, 50, 60, 70, 80, 90, 100 are detected. 20 people at the same age are randomly selected for sampling, and the samples are centrifuged and diluted and then added into the chamber for detection;

(2) the statistics on detection results for each age group are conducted: the blocking current and blocking time corresponding to the peaks are taken as two characteristic values for this age group, and the "age-blocking current curve" and the "age-duration times curve" are drawn respectively;

(3) the samples of unknown age to be detected are centrifuged and diluted and then added into the chamber, the statistics on the blocking current and the duration times are conducted. The age of the samples can be obtained corresponding to the "age-blocking current curve" and the "age-blocking time curve".

Application Example 7

The Micro-RNA detection can be carried out via an aerolysin nanopore.

Micro-RNA has the role of regulating the expression of genes in the human body, with the Micro-RNA levels in the human body directly related to various diseases. The latest studies show that the levels of Micro-RNA-21-5P and Micro-RNA-92a-3P in rectal cancer patients are on the rise. The application of the aerolysin nanopore in the disclosure not only distinguishs various Micro-RNAs, but also enables the quantitative detection of actual samples so that the level of Micro-RNA in actual samples can be detected at the single molecule level specificity without labeling for the clinical diagnosis of diseases.

The Micro-RNA sequences to be tested are as follows:

```
Micro-RNA21:
UAGCUUAUCAGACUGAUGUUGA;

Micro-RNA92:
UAUUGCACUUGUCCCGGCCUGU.
```

The step of detection more specifically comprises the sub-steps of:

(1) the Micro-RNA21 and the Micro-RNA92 with the same concentration are added into the chamber, and the statistics on the current signals generated by three kinds of Micro-RNAs are conducted;

(2) the Micro-RNA21 and the Micro-RNA92 with different concentrations are measured, and the concentrations should be linear with the frequency of signals;

(3) the samples to be detected are centrifuged and then added into the chamber; based on the concentration-frequency curve measured in Step (1), the level of Micro-RNAs in the sample to be detected can be obtained for the early diagnosis of diseases.

Notably, the foregoing are only preferable embodiments of the disclosure. It will be apparent to those skilled in the art that certain improvements and modifications may be made without departing from the method of the disclosure, and that such improvements and modifications are included in the scope of the disclosure.

What is claimed is:

1. A preparation method for an aerolysin nanopore, comprising the following steps:
   (1) pretreatment of an aerolysin, in which:
      a trypsin-ethylenediaminetetraacetic acid (EDTA) solution and the aerolysin are mixed at a ratio of 1:100 and incubated at room temperature for 10 min to activate the aerolysin, and the activated aerolysin is treated in a phosphate-buffered saline (PBS) buffer and stored in a refrigerator at −20° C. at a concentration ranging from 0.1 to 10 mg/ml;
   (2) preparation of a lipid bilayer membrane by pulling process, in which:
      the lipid bilayer membrane is formed at a polyacetal resin chamber as a carrier, wherein the polyacetal resin chamber comprises chamber I (cis chamber) and chamber II (trans chamber), with the chamber II embedded in the chamber I; the polyacetal resin chamber is divided into two regions after the lipid bilayer membrane is formed; as the aerolysin nanopore is unidirectional when embedded into the lipid bilayer membrane, the region corresponding to a relatively large opening of the aerolysin nanopore embedded in the lipid bilayer membrane is defined as the chamber I while the other region, corresponding to a relatively small opening of the aerolysin nanopore, is defined as the chamber II; the chamber II is provided with a small pore with a diameter of 50 μm, wherein the small pore is configured for forming the lipid bilayer membrane; the chamber I is provided in a lateral side thereof with a pulling pore in communication with an interior of the chamber I, wherein the pulling pore is configured for insertion by an injector for pulling an internal solution; and a 1,2-diglycanoyl phospholipid to be used for forming the lipid bilayer membrane is stored in a chloroform solution in a refrigerator at −20° C.;
      the step of preparation of the lipid bilayer membrane more specifically comprising the sub-steps of:
      (a) drying the chloroform in the 1,2-diglycanoyl phospholipid chloroform solution and adding 90 μl of n-decane into the chloroform-removed 1,2-diglycanoyl phospholipid to prepare a phospholipid n-decane solution, prior to the step of preparation of the lipid bilayer membrane;
      (b) smearing the phospholipid n-decane solution evenly on both internal and external sides of the small pore of the chamber 2 of 1 mL with a sable paint brush and drying the applied phospholipid n-decane solution with a flow of $N_2$ to form a lipid bilayer membrane;
      (c) putting the chamber I and the chamber II together, adding 1 mL of an electrolyte solution into each the chamber, immersing a pair of Ag/AgCl electrodes into the electrolyte solution, and applying a potential of 100-300 mV across lipid bilayer membrane via output ends of a current amplifier, wherein the cis chamber is defined as a virtual ground;
      (d) pulling the electrolyte solution repeatedly to form the lipid bilayer membrane at the small pore of the trans chamber; monitoring the quality of the formed lipid bilayer membrane via capacitance, applying a potential of 400 mV to examine a thickness of the lipid bilayer during formation of the lipid bilayer membrane;
      (e) breaking the lipid bilayer membrane under the potential of 400 mV, pulling the electrolyte to form another lipid bilayer membrane, wherein the capacitance of the another lipid bilayer membrane is equal to or higher than the capacitance of the broken lipid bilayer membrane, and the another lipid bilayer membrane capable of forming a nanopore is obtained;
   (3) formation of the aerolysin nanopore, in which:
      1-10 μl of the aerolysin is added into the cis chamber after a stable the lipid bilayer membrane is formed, and a potential is applied to embed the aerolysin into the lipid bilayer membrane; the ionic current increases abruptly when the aerolysin forms a stable nanopore in the lipid bilayer membrane; at the same time, the aerolysin nanopore at a current of 50±5 pA under a potential of 100 mV can be obtained.

2. The method for preparing an aerolysin nanopore as claimed in claim 1, wherein the range of the potential applied in Step (3) is 100 mV.

3. The method for preparing an aerolysin nanopore as claimed in claim 1, wherein more than one nanopore can be obtained simultaneously via the preparation method, and wherein the insertion of a nanopore corresponds to the current increase of 50±5 pA under a potential of 100 mV.

* * * * *

SEQUENCE LISTING

```
<160> NUMBER OF SEQ ID NOS: 2

<210> SEQ ID NO 1
<211> LENGTH: 22
<212> TYPE: RNA
<213> ORGANISM: Homo sapiens

<400> SEQUENCE: 1
uagcuuauca gacugauguu ga                                             22

<210> SEQ ID NO 2
<211> LENGTH: 22
<212> TYPE: RNA
<213> ORGANISM: Homo sapiens

<400> SEQUENCE: 2
uauugcacuu gucccggccu gu                                             22
```